(12) United States Patent
Timothy Donald et al.

(10) Patent No.: US 8,366,669 B2
(45) Date of Patent: Feb. 5, 2013

(54) INJECTION DEVICE

(75) Inventors: Barrow-Williams Timothy Donald, St. Albans (GB); Edington David, St. Albans (GB)

(73) Assignee: Cilag GmbH International (CH)

( * ) Notice: Subject to any disclaimer, the term of this patent is extended or adjusted under 35 U.S.C. 154(b) by 143 days.

(21) Appl. No.: 11/910,545

(22) PCT Filed: Mar. 21, 2006

(86) PCT No.: PCT/GB2006/001031
§ 371 (c)(1),
(2), (4) Date: May 29, 2008

(87) PCT Pub. No.: WO2006/106295
PCT Pub. Date: Oct. 12, 2006

(65) Prior Publication Data
US 2009/0088688 A1   Apr. 2, 2009

(30) Foreign Application Priority Data
Apr. 6, 2005   (GB) .................................. 0507016.4

(51) Int. Cl.
*A61M 37/00*   (2006.01)
(52) U.S. Cl. ........................................................ 604/136
(58) Field of Classification Search ................... 604/136
See application file for complete search history.

(56) References Cited

U.S. PATENT DOCUMENTS

| | | |
|---|---|---|
| 1,845,036 A | 2/1932 | Busher |
| 2,019,382 A | 10/1935 | Aronson |
| 2,531,267 A | 11/1950 | Harisch |
| 2,764,977 A | 10/1956 | Ferguson |
| 2,828,742 A | 4/1958 | Ashkenaz |
| 3,329,146 A | 7/1967 | Waldman |
| 3,543,603 A | 12/1970 | Gley |
| 3,656,472 A | 4/1972 | Ben Moura |
| 3,702,608 A | 11/1972 | Tibbs |

(Continued)

FOREIGN PATENT DOCUMENTS

| | | |
|---|---|---|
| CH | 518102 A | 1/1972 |
| CN | 2059579 U | 7/1990 |

(Continued)

OTHER PUBLICATIONS

International Search Report dated Sep. 5, 2005; International Application No. PCT/GB2005/002117.

(Continued)

*Primary Examiner* — Nicholas D Lucchesi
*Assistant Examiner* — Diva Ranade

(57) ABSTRACT

An injection device (110) comprises a housing (112) adapted to receive a syringe (116) having a discharge nozzle (118) and dispensing piston (114) movable in the syringe to expel the contents of the syringe through the discharge nozzle. There is also a drive (130) adapted to act on the syringe to advance it from a retracted position in which the discharge nozzle is contained within the housing to an extended position in which the discharge nozzle extends from housing. A drive coupling (134) extends from the drive to the dispensing piston of the syringe so as to transfer movement of the drive to the piston. The drive coupling comprises a fixed-length drive-coupling and an interchangeable drive coupling. There is also a method of manufacturing an injection device by assembling a first sub-assembly (210) and second sub-assembly (220).

12 Claims, 4 Drawing Sheets

U.S. PATENT DOCUMENTS

| | | |
|---|---|---|
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,231,368 A | 11/1980 | Becker |
| 4,299,238 A | 11/1981 | Baidwan et al. |
| 4,378,015 A | 3/1983 | Wardlaw |
| 4,394,863 A | 7/1983 | Bartner |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,636,201 A | 1/1987 | Ambrose et al. |
| 4,744,786 A | 5/1988 | Hooven et al. |
| 4,787,891 A | 11/1988 | Levin et al. |
| 4,874,383 A | 10/1989 | McNaughton |
| 4,929,232 A | 5/1990 | Sweeney et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,156,599 A | 10/1992 | Ranford et al. |
| 5,176,643 A | 1/1993 | Kramer et al. |
| 5,190,526 A | 3/1993 | Murray et al. |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,330,430 A | 7/1994 | Sullivan |
| 5,358,489 A | 10/1994 | Wyrick |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,514,097 A | 5/1996 | Knauer |
| 5,520,653 A | 5/1996 | Reilly et al. |
| 5,540,660 A | 7/1996 | Jenson et al. |
| 5,540,709 A | 7/1996 | Ramel et al. |
| 5,567,160 A | 10/1996 | Massino |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,609,577 A | 3/1997 | Haber et al. |
| 5,609,584 A | 3/1997 | Gettig et al. |
| 5,637,094 A | 6/1997 | Stewart, Jr. et al. |
| 5,645,536 A | 7/1997 | Whisson |
| 5,647,845 A | 7/1997 | Haber et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,843,036 A | 12/1998 | Olive et al. |
| 5,868,711 A | 2/1999 | Kramer et al. |
| 5,879,327 A | 3/1999 | DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,159,181 A | 12/2000 | Crossman et al. |
| 6,162,199 A | 12/2000 | Geringer |
| 6,171,276 B1 | 1/2001 | Markus et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,293,925 B1 | 9/2001 | Safabash et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydlon et al. |
| 6,461,333 B1 | 10/2002 | Frezza |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1* | 2/2004 | Weekes et al. .......... 604/197 |
| 6,699,220 B2 | 3/2004 | Rolfe |
| 6,740,062 B2 | 5/2004 | Hjertman |
| 6,743,199 B2 | 6/2004 | Shue et al. |

| | | |
|---|---|---|
| 6,743,203 B1 | 6/2004 | Pickhard |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,634 B2 | 8/2006 | Gilbert |
| 7,118,553 B2 | 10/2006 | Scherer |
| 7,156,823 B2 | 1/2007 | Landau et al. |
| 7,744,561 B2 | 6/2010 | Stamp |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0173752 A1 | 11/2002 | Polzin |
| 2002/0183690 A1 | 12/2002 | Arnisolle |
| 2003/0036679 A1 | 2/2003 | Kortenbach et al. |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1* | 6/2003 | Dedig et al. ............... 604/151 |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0015134 A1 | 1/2004 | Lavi et al. |
| 2004/0019326 A1 | 1/2004 | Gilbert et al. |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0203466 A1 | 9/2005 | Hommann et al. |
| 2005/0215941 A1* | 9/2005 | Bernard et al. ............... 604/20 |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184137 A1 | 8/2006 | Reynolds |
| 2006/0224124 A1 | 10/2006 | Scherer |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0078382 A1 | 4/2007 | Hommann et al. |
| 2007/0142787 A1 | 6/2007 | Scherer |
| 2008/0312606 A1 | 12/2008 | Harrison et al. |
| 2009/0054849 A1 | 2/2009 | Burnell et al. |
| 2009/0088688 A1* | 4/2009 | Timothy Donald et al. .. 604/136 |
| 2010/0016793 A1 | 1/2010 | Jennings et al. |

FOREIGN PATENT DOCUMENTS

| | | |
|---|---|---|
| CN | 1190599 A | 8/1998 |
| CN | 1541121 A | 10/2004 |
| CN | 1550240 A | 12/2004 |
| DD | 229932 A1 | 11/1985 |
| DE | 902776 C | 1/1954 |
| DE | 3604826 A1 | 10/1986 |
| DE | 4428467 A1 | 2/1996 |
| DE | 29513214 U1 | 1/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 | 10/1987 |
| EP | 0482677 | 4/1992 |
| EP | 0516473 | 12/1992 |
| EP | 0331452 A2 | 8/1993 |
| EP | 0585626 A1 | 3/1994 |
| EP | 0389938 B1 | 5/1994 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |

| | | | | | | |
|---|---|---|---|---|---|---|
| EP | 0666084 B1 | 4/2004 | | WO | 88/10129 A1 | 12/1988 |
| EP | 0941133 B1 | 4/2004 | | WO | 98/10129 A1 | 12/1988 |
| EP | 1124601 B1 | 12/2004 | | WO | 92/19296 A | 11/1992 |
| EP | 1518575 | 3/2005 | | WO | 93/02186 A1 | 2/1993 |
| EP | 1364667 B1 | 4/2005 | | WO | 93/23098 A1 | 11/1993 |
| EP | 1208858 B1 | 6/2006 | | WO | WO 93/21986 A2 | 11/1993 |
| EP | 1755710 A1 | 2/2007 | | WO | 94/04207 A1 | 3/1994 |
| EP | 1586341 B1 | 1/2008 | | WO | WO 94/07554 A1 | 4/1994 |
| EP | 1932558 A1 | 6/2008 | | WO | WO 94/11041 | 5/1994 |
| EP | 2023980 A1 | 2/2009 | | WO | 94/13342 A1 | 6/1994 |
| EP | 2129414 A1 | 12/2009 | | WO | 94/21316 A1 | 9/1994 |
| EP | 1755706 B1 | 3/2010 | | WO | WO 94/22511 | 10/1994 |
| EP | 1928523 B1 | 7/2010 | | WO | 95/04562 A1 | 2/1995 |
| FR | 1014881 A | 8/1952 | | WO | 95/29720 A1 | 11/1995 |
| FR | 1169935 | 1/1959 | | WO | 95/31235 A1 | 11/1995 |
| FR | 1538565 A | 9/1968 | | WO | 95/35126 A1 | 11/1995 |
| FR | 2506161 A1 | 11/1982 | | WO | WO 95/35126 | 12/1995 |
| FR | 2629706 A | 10/1989 | | WO | 96/30065 A1 | 10/1996 |
| FR | 2654938 A1 | 5/1991 | | WO | 97/10865 A1 | 3/1997 |
| FR | 2665079 A1 | 1/1992 | | WO | 97/13538 A1 | 4/1997 |
| FR | 2717086 A1 | 9/1995 | | WO | 97/48430 A1 | 12/1997 |
| FR | 2741810 A1 | 6/1997 | | WO | 98/11927 A1 | 3/1998 |
| FR | 2861310 A1 | 4/2005 | | WO | 99/03529 A2 | 1/1999 |
| GB | 143084 | 5/1920 | | WO | 99/10030 A2 | 3/1999 |
| GB | 0412054 | 6/1934 | | WO | 99/22789 A1 | 5/1999 |
| GB | 728248 | 4/1955 | | WO | 99/37343 A | 7/1999 |
| GB | 909898 | 11/1962 | | WO | 99/53979 A1 | 10/1999 |
| GB | 1263355 | 2/1972 | | WO | 99/59658 A1 | 11/1999 |
| GB | 1311937 A | 3/1973 | | WO | 00/06227 A1 | 2/2000 |
| GB | 1514725 | 6/1978 | | WO | 00/07539 A1 | 2/2000 |
| GB | 2338033 A | 12/1999 | | WO | 00/13723 A2 | 3/2000 |
| GB | 2396298 A | 6/2004 | | WO | 00/24441 A1 | 5/2000 |
| GB | 2396816 A | 7/2004 | | WO | 00/35516 | 6/2000 |
| GB | 2397767 A | 8/2004 | | WO | 00/50107 A1 | 8/2000 |
| GB | 2414398 A | 11/2005 | | WO | 00/64515 A1 | 11/2000 |
| GB | 2414399 A | 11/2005 | | WO | 00/69488 A2 | 11/2000 |
| GB | 2414400 A | 11/2005 | | WO | 01/05456 A1 | 1/2001 |
| GB | 2414401 A | 11/2005 | | WO | 01/49347 A1 | 7/2001 |
| GB | 2414402 | 11/2005 | | WO | 01/76666 A1 | 10/2001 |
| GB | 2414403 | 11/2005 | | WO | 01/77384 A2 | 10/2001 |
| GB | 2424835 A | 10/2006 | | WO | 01/87384 A1 | 11/2001 |
| GB | 2424836 A | 10/2006 | | WO | 02/11799 A1 | 2/2002 |
| GB | 2424838 A | 10/2006 | | WO | 02/47746 A1 | 6/2002 |
| GB | 2433035 A | 6/2007 | | WO | WO 02/056947 | 7/2002 |
| GB | 2437922 A | 11/2007 | | WO | 03/013632 A2 | 2/2003 |
| GB | 2438591 A | 12/2007 | | WO | 03/015853 A1 | 2/2003 |
| GB | 2446778 A | 8/2008 | | WO | 03/039633 A2 | 5/2003 |
| JP | 59-115053 A | 7/1984 | | WO | 03/041768 A | 5/2003 |
| JP | 2-185261 A | 7/1990 | | WO | 03/047663 A2 | 6/2003 |
| JP | 2-502971 T | 9/1990 | | WO | 03/051434 A2 | 6/2003 |
| JP | 11-501549 T | 2/1992 | | WO | 03/066141 A1 | 8/2003 |
| JP | 5-161712 | 6/1993 | | WO | 03/092771 | 11/2003 |
| JP | 6-209996 A | 8/1994 | | WO | 03/097133 | 11/2003 |
| JP | 6-508773 T | 10/1994 | | WO | 03/099358 A2 | 12/2003 |
| JP | 6-327770 A | 11/1994 | | WO | 2004/007554 A1 | 1/2004 |
| JP | 7-222799 A | 8/1995 | | WO | 2004/011065 A1 | 2/2004 |
| JP | 8-502180 T | 3/1996 | | WO | 2004/030732 A2 | 4/2004 |
| JP | 8-504354 T | 5/1996 | | WO | 2004/035117 A2 | 4/2004 |
| JP | 9-225029 A | 9/1997 | | WO | 2004/047890 A1 | 6/2004 |
| JP | 10-504474 T | 5/1998 | | WO | 2004/047891 A1 | 6/2004 |
| JP | 10-507935 A | 8/1998 | | WO | 2004/047892 A | 6/2004 |
| JP | 11-503637 T | 3/1999 | | WO | 2004/054644 A1 | 7/2004 |
| JP | 11-504536 T | 4/1999 | | WO | 2004/054645 A3 | 7/2004 |
| JP | 11-164887 T | 6/1999 | | WO | 2004/087242 A1 | 10/2004 |
| JP | 11-512332 T | 10/1999 | | WO | 2004/108194 A1 | 12/2004 |
| JP | 2000-510021 T | 8/2000 | | WO | 2005/009515 A1 | 2/2005 |
| JP | 2002-500933 T | 1/2002 | | WO | 2005/025636 A2 | 3/2005 |
| JP | 2002-095749 A | 4/2002 | | WO | WO 2005/023341 A1 | 3/2005 |
| JP | 2002-513547 T | 5/2002 | | WO | WO 2005/030301 A1 | 4/2005 |
| JP | 2002-526175 A | 8/2002 | | WO | WO 2005/035028 A1 | 4/2005 |
| JP | 2002-528182 T | 9/2002 | | WO | 2005/044345 A | 5/2005 |
| JP | 2002-532161 T | 10/2002 | | WO | WO 2005/044347 A1 | 5/2005 |
| JP | 2003-511105 T | 3/2003 | | WO | 2005/058396 A1 | 6/2005 |
| JP | 2003-532500 T | 11/2003 | | WO | 2005/070481 A1 | 8/2005 |
| JP | 2003-533288 A | 11/2003 | | WO | 2005/082438 A1 | 9/2005 |
| JP | 2004-533282 T | 11/2004 | | WO | 2005/097238 A3 | 10/2005 |
| JP | 2004-33737 A | 8/2005 | | WO | 2005/115508 A1 | 12/2005 |
| NZ | 573171 A | 11/2010 | | WO | 2005/115509 A1 | 12/2005 |
| NZ | 573350 A | 12/2010 | | WO | 2005/115510 A1 | 12/2005 |

| | | |
|---|---|---|
| WO | 2005/115512 A1 | 12/2005 |
| WO | 2005/115513 A1 | 12/2005 |
| WO | 2005/120607 A2 | 12/2005 |
| WO | WO 2005/115507 A1 | 12/2005 |
| WO | WO 2005/115514 A1 | 12/2005 |
| WO | 2006/044236 A2 | 4/2006 |
| WO | WO 2006/050304 A1 | 5/2006 |
| WO | 2006/062788 A2 | 6/2006 |
| WO | 2006/063015 A2 | 6/2006 |
| WO | 2006/063124 A2 | 6/2006 |
| WO | 2006/088513 A1 | 8/2006 |
| WO | 2006/088630 A2 | 8/2006 |
| WO | 2006/099441 A2 | 9/2006 |
| WO | 2006/106290 A1 | 10/2006 |
| WO | 2006/106294 A | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106295 A1 | 10/2006 |
| WO | 2006/118616 A1 | 11/2006 |
| WO | WO 2006/129196 A1 | 12/2006 |
| WO | 2007/027204 A2 | 3/2007 |
| WO | 2007/036676 A1 | 4/2007 |
| WO | 2007/047200 A1 | 4/2007 |
| WO | 2007/051330 A1 | 5/2007 |
| WO | 2007/066152 A | 6/2007 |
| WO | 2007/122193 A1 | 11/2007 |
| WO | 2007/131013 A | 11/2007 |
| WO | 2007/138299 A1 | 12/2007 |
| WO | 2008/047372 A2 | 4/2008 |
| WO | 2008/075033 A | 6/2008 |
| WO | 2008/093063 A2 | 8/2008 |
| WO | WO 88/08725 | 11/2008 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.

* cited by examiner

INJECTION DEVICE

FIELD OF THE INVENTION

The present invention relates to an injection device of the type that receives a syringe, extends it, discharges its contents and then retracts it automatically.

BACKGROUND OF THE INVENTION

Known injection devices are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Generally, such injection devices require a high force drive spring in order to reliably empty the syringe in the time before retraction of the syringe. When the drive spring is first released, the spring first takes up clearance in the syringe, then extends the syringe and needle and then delivers the drug. The spring force is significantly higher than that required for these initial steps and excess energy is liberated in the form of noise and vibration resulting from recoil of the spring.

An injection device can generally operate with a range of syringe fill volumes. When the fill volume is low, there can be substantial clearance to be taken up and hence louder noise and higher recoil on actuation.

It is therefore desirable to minimise the noise and recoil to avoid startling the patient for a range of syringe fill volumes.

SUMMARY OF THE INVENTION

The injection device of the present invention is designed to deal with the aforementioned problem and other issues.

In view of the foregoing and in accordance with a first aspect of the present invention, there is provided an injection device comprising:
  a housing adapted to receive a syringe having a discharge nozzle and a dispensing piston movable in the syringe to expel the contents of the syringe through the discharge nozzle;
  a drive adapted on activation to act on the syringe to advance it from a retracted position in which the discharge nozzle is contained within the housing to an extended position in which the discharge nozzle extends from the housing;
  a drive coupling for extending from the drive to the dispensing piston of the syringe so as to transfer movement of the drive to the piston,
  characterised in that the drive coupling comprises a fixed-length drive coupling and an interchangeable drive coupling.

By varying the length of the interchangeable drive coupling, the noise and vibration resulting from actuation of the device can be minimised for a given volume of contents in the syringe.

Preferably, the interchangeable drive coupling comprises a rigid member configured to connect with the dispensing piston and with the fixed-length drive coupling.

The rigid member has a longitudinal axis.

Advantageously, the quantity of the contents of the syringe which is expelled in use determines the length of the interchangeable drive coupling along its longitudinal axis.

Generally, the length of the interchangeable drive coupling is inversely proportional to the quantity of the contents of the syringe.

In one embodiment of the present invention, there is provided an interchangeable release element adapted to disengage the drive from the fixed-length drive coupling after a predetermined amount of movement of the piston.

Preferably, the interchangeable release element is a constriction adapted to act on at least one arm linking the fixed-length drive coupling to the drive, thereby releasing the drive from the fixed-length drive coupling.

Advantageously, the length of the constriction determines the predetermined amount of movement of the piston.

Generally, the length of the constriction is inversely proportional to the quantity of the contents of the syringe.

In accordance with a second aspect of the invention, there is provided a method of manufacturing an injection device, comprising:
  inserting a syringe having a piston into a first sub-assembly;
  inserting an interchangeable drive coupling into the syringe to contact the piston;
  providing a second sub-assembly comprising a drive and a fixed-length drive coupling; and
  assembling the first sub-assembly and second sub-assembly together,
  wherein, on assembly, the fixed-length drive coupling and interchangeable drive coupling communicate in use to transfer movement of the drive to the piston.

Preferably, the interchangeable component has a longitudinal axis and comprises a rigid member configured to connect with the piston and with the drive coupling.

In one embodiment of the present invention, there is the additional step of selecting the interchangeable drive coupling in accordance with its length determined by the quantity of the contents of the syringe.

In a further embodiment of the present invention, there is the further step of connecting an interchangeable release element to the first sub-assembly before the step of assembling, wherein the interchangeable release element is adapted to actuate after a predetermined amount of movement of the piston a delay mechanism in the drive acting on the fixed-length drive coupling.

Preferably, the interchangeable release element is selected in accordance with its length determined by the quantity of the contents of the syringe.

BRIEF DESCRIPTION OF THE DRAWINGS

The invention will now be described by way of example with reference to the accompanying drawings, in which.

DETAILED DESCRIPTION OF THE DRAWINGS

Figure 1:
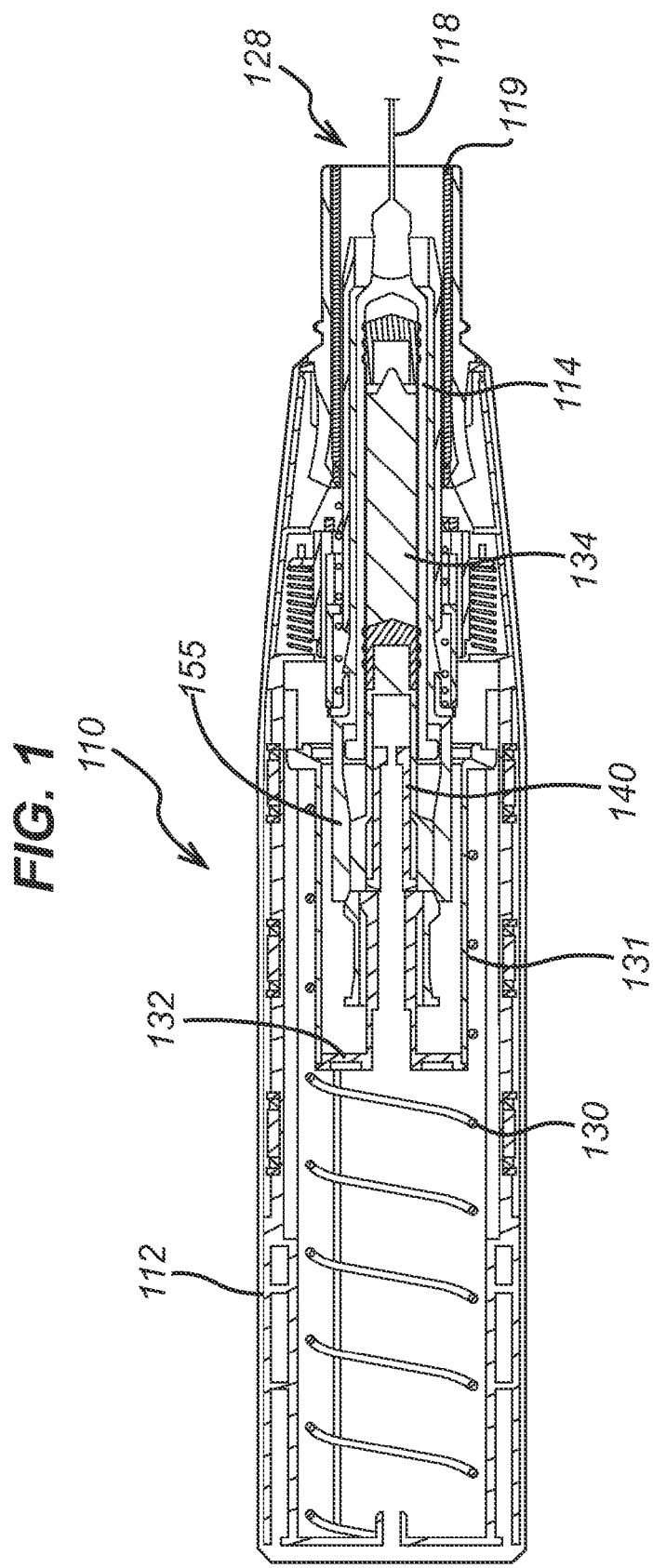
FIG. 1 shows a cross-sectional view of an injection device according to the present invention.
Figure 2:
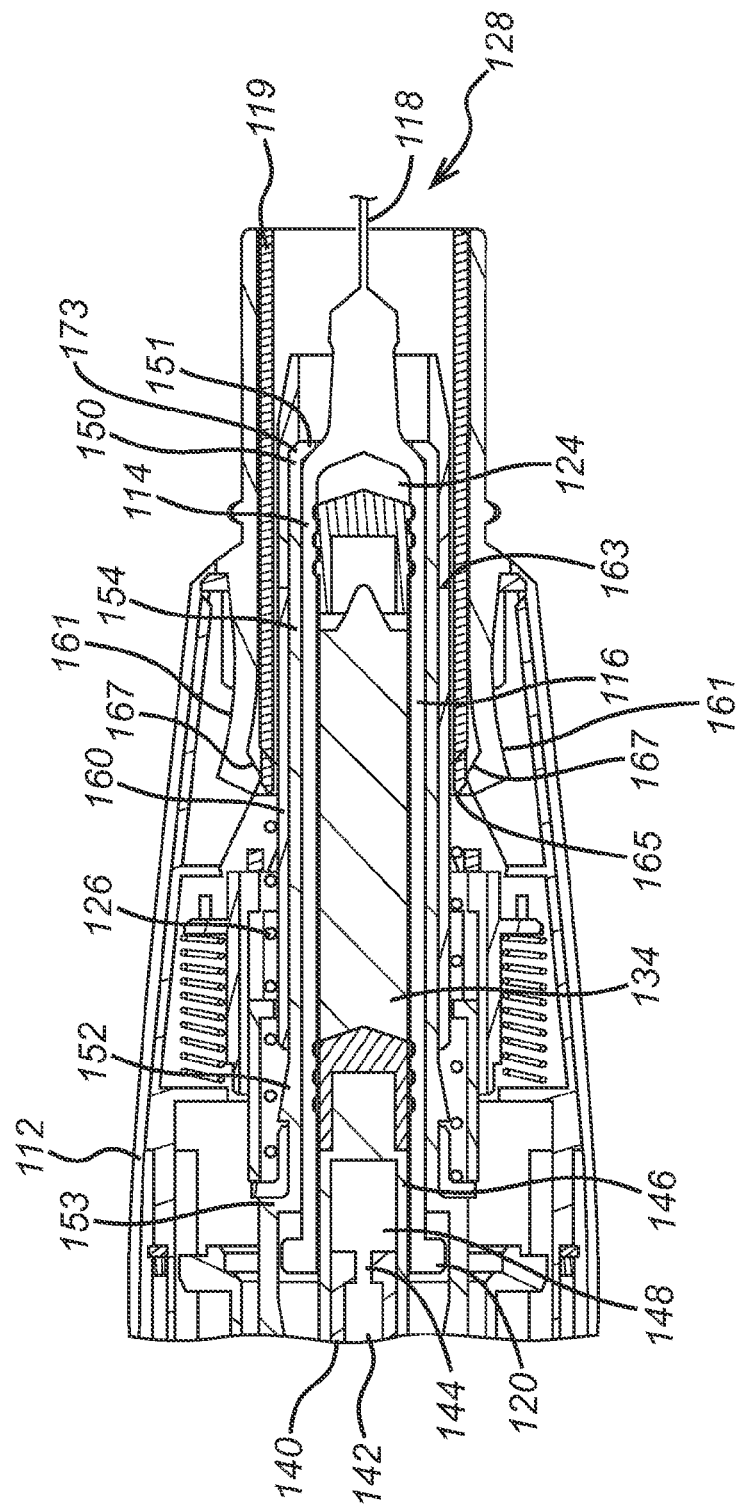
FIG. 2 shows an enlarged part of the injection device shown in FIG. 1.

FIGS. 1 to 4 show an injection device 110, having an injection device housing 112. The end of the housing 112 has an exit aperture 128, through which the end of a sleeve 119 can emerge.

The housing 112 contains a hypodermic syringe 114 of conventional type, including a syringe body 116 defining a reservoir and terminating at one end in a hypodermic needle 118 and at the other in a flange 120. The syringe body 116 is of substantially constant diameter along the length of the reservoir, and is of significantly smaller diameter close to the end of the syringe which terminates in the hypodermic needle. A drive coupling 134 acts through the bung of the syringe to discharge the contents of the syringe 114 through the needle 118. This drive coupling 134 constrains a drug 124 to be administered within the reservoir defined by syringe body 116. Whilst the syringe illustrated is of hypodermic type, this need not necessarily be so. Transcutaneous or ballistic dermal and subcutaneous syringes may also be used with the injection device of the present invention.

As illustrated, the syringe is housed within a syringe carrier 150. The syringe carrier 150 has a proximal end 151 through which the needle 118 of the syringe protrudes. The needle 118 is attached to the syringe body 116 of the syringe by a needle sub-assembly 172 which has a reduced diameter. At the proximal end 151 of the syringe carrier 150, there is a section of reduced diameter 173 which supports the end of the syringe 114 on its body 116. The syringe carrier 150 also includes a pair of flexible projections 152. The pair of flexible projections 152 communicate with a corresponding pair of locking apertures on a return spring support 160 so that the syringe carrier 150 cannot move relative to the return spring support 160. The syringe carrier 150 also comprises a bearing surface 153 close to its second end, against which a corresponding bearing surface of the return spring support 160 is biased by a return spring 126. The return spring 126, via the return spring support 160 and the syringe carrier 150 biases the syringe 114 from an extended position in which the needle 118 extends from the aperture 128 in the housing 112 to a retracted position in which the needle 118 is contained within the housing 112.

The syringe carrier 150 comprises a sheath 154 into which the syringe 114 can be inserted from a distal end 170. The syringe 114 is provided with a boot (not shown). If the syringe were to fail or break, the sheath 154, which surrounds the syringe 114 along its length, would contain the broken pieces of syringe and reduce the likelihood of them from escaping from the injection device 110.

The housing is further provided with a resilient latch member 161 that is biased into a position in which it engages a locking surface 163 on the return spring support 160. Before engaging the locking surface 163, the latch member 161 also extends through a latch opening 165 in the sleeve 119. The latch member 161 includes a ramped surface 167 against which an edge of the latch opening 165 acts in the manner of a cam acting on a cam follower.

The housing also includes an actuator, and a drive which here takes the form of a compression drive spring 130. Drive from the drive spring 130 is transmitted via a multi-component drive to the piston of the syringe 114 to advance the syringe from its retracted position to its extended position and discharge its contents through the needle 118. The drive accomplishes this task by acting directly on the drug 124 and the syringe 114. Static friction between the drive coupling 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a drive element 132. This in turn transmits drive to the drive coupling 134 already mentioned.

The drive element 132 includes a hollow stem 140, the inner cavity of which forms a collection chamber 142 in communication with a vent 144 that extends from the collection chamber through the end of the stem 140. The drive coupling 134 includes a blind bore 146 that is open at one end to receive the stem 140 and closed at the other. As can be seen, the bore 146 and the stem 140 define a fluid reservoir 148, within which a damping fluid is contained.

A trigger 214 is provided on the housing 112 remote from the exit aperture 128. The trigger, when operated, serves to decouple the drive sleeve 131 from the housing 112, allowing it to move relative to the housing 112 under the influence of the drive spring 130. The operation of the device is then as follows.

Initially, the return spring carrier 152, and consequently the syringe carrier 150 and syringe 114, are prevented from movement by the resilient latch member 161. By moving the sleeve 119 in a direction into the housing 112, the edge of the latch opening 165 is brought into contact with the ramped surface 167 of the latch member 161, causing the latch member 161 to move outwards and thus to disengage from the return spring support 160. Once the latch member 161 has disengaged from the locking surface 163, the syringe is free to move.

The actuator is then depressed and the drive spring 130 is released. The drive spring 130 moves the drive sleeve 131, the drive sleeve 131 moves the drive element 132 and the drive element 132 moves the drive coupling 134. The drive coupling 134 moves and, by virtue of static friction and hydrostatic forces acting through the drug 124 to be administered, moves the syringe body 114 against the action of the return spring 126. The syringe body 114 moves the syringe carrier 150, which in turn moves the return spring support 160 and compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the drive coupling 134 and the syringe body 116 and the hydrostatic forces acting through the drug 124 to be administered are not sufficient to resist the fill drive force developed by the drive spring 130, at this point the drive coupling 134 begins to move within the syringe body 116 and the drug 124 begins to be discharged. Dynamic friction between the drive coupling 134 and the syringe body 116 and hydrostatic and hydrodynamic forces now acting through the drug 124 to be administered are, however, sufficient to retain the return spring 126 in its compressed state, so the hypodermic needle 118 remains extended.

Before the drive coupling 134 reaches the end of its travel within the syringe body 116, so before the contents of the syringe have fully discharged, flexible latch arms linking the first and drive couplings 132, 134 reach an interchangeable release element 155 connected to the distal end of the syringe carrier 150.

The interchangeable release element 155 is essentially a constriction which moves the flexible latch arms to a position so that they no longer couple the drive element 132 to the drive coupling 134. Once this happens, the drive element 132 acts no longer on the drive coupling 134, allowing the drive element 132 to move relative to the drive coupling 134.

Because the damping fluid is contained within a reservoir 148 defined between the end of the drive element 132 and the blind bore 146 in the drive coupling 134, the volume of the reservoir 146 will tend to decrease as the drive element 132 moves relative to the drive coupling 134 when the former is acted upon by the drive spring 130. As the reservoir 148 collapses, damping fluid is forced through the vent 144 into the collection chamber 142. Thus, once the flexible latch arms have been released, some of the force exerted by the drive spring 130 does work on the damping fluid, causing it to flow though the constriction formed by the vent 144; the remainder acts hydrostatically through the fluid and through friction between the first and drive couplings 132, 134, thence via the drive coupling 134. Consequently, the drive coupling 134 continues to move within the syringe body 116 and the drug 124 continues to be discharged. Losses associated with the flow of the damping fluid do not attenuate the force acting on the body of the syringe to a great extent. Thus, the return spring 126 remains compressed and the hypodermic needle remains extended.

After a time, the drive coupling 134 completes its travel within the syringe body 116 and can go no further. At this point, the contents of the syringe 114 are completely discharged and the force exerted by the drive spring 130 acts to retain the drive coupling 134 in its terminal position and to continue to cause the damping fluid to flow though the vent 144, allowing the drive element 132 to continue its movement.

Before the reservoir 148 of fluid is exhausted, flexible latch arms linking the drive sleeve 131 with the drive element 132 reach another constriction within the housing 112. The constriction moves the flexible latch arms so that they no longer couple the drive sleeve 131 to the drive element 132. Once this happens, the drive sleeve 131 acts no longer on the drive element 132, allowing them to move relative each other. At this point, the forces developed by the drive spring 130 are no longer being transmitted to the syringe 114. The only force acting on the syringe will be the return force from the return spring 126 which acts on the end of the syringe 114 nearest to the needle 118 via the return spring support 160 and the syringe carrier 150. Consequently, the syringe is returned to its retracted position and the injection cycle is complete.

Figure 3:
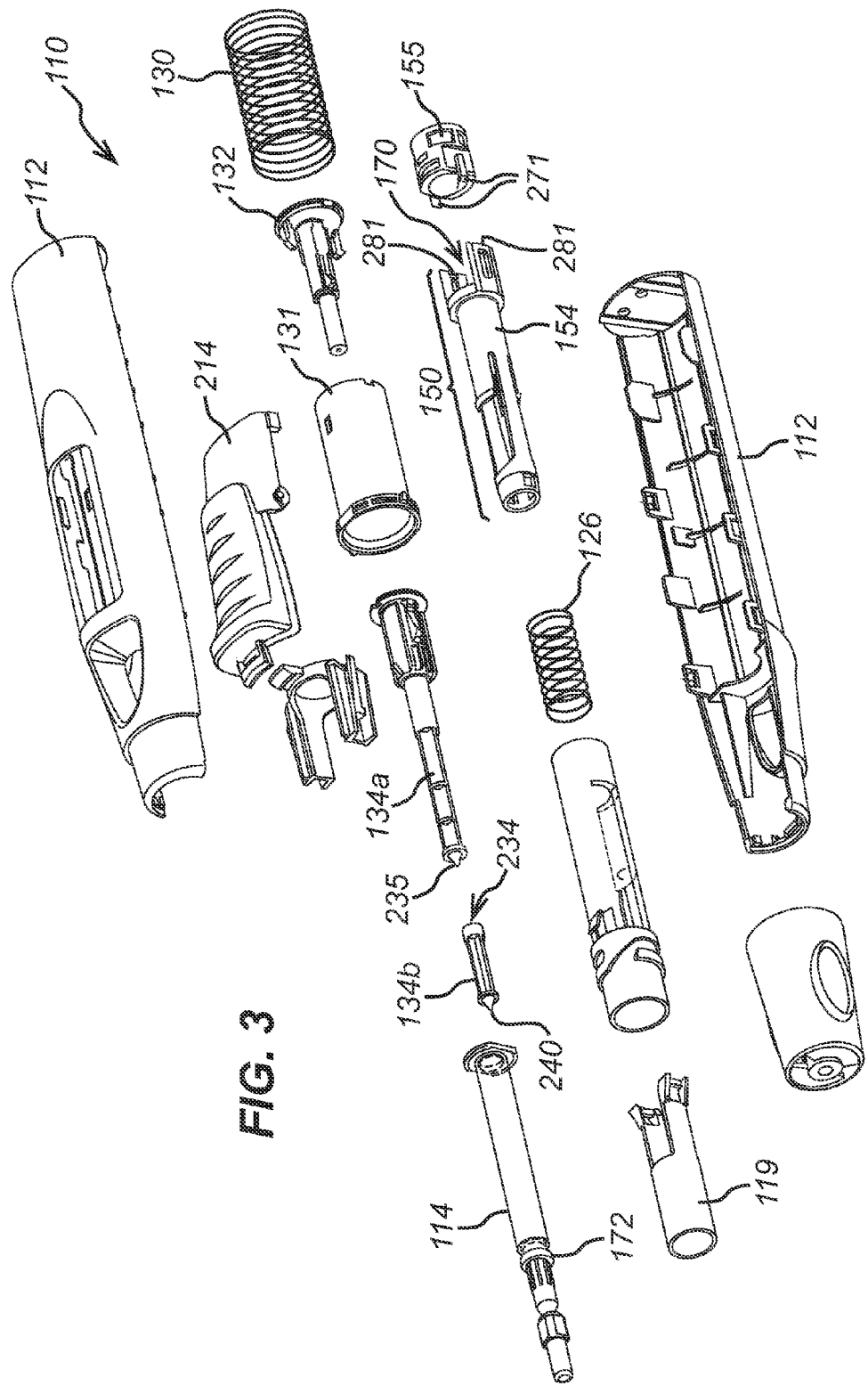
FIG. 3 shows an exploded view of components of the injection device according to the present invention.

As can be seen from FIG. 3, the drive coupling 134 comprises a fixed-length drive coupling 134a and an interchangeable drive coupling 134b. The length of the interchangeable drive coupling 134b can be varied by changing it for a different interchangeable drive coupling. The interchangeable drive coupling 134b includes a cup 234 at its end adjacent the fixed-length drive coupling 134a for receiving a protrusion 235 on the fixed-length coupling 134b.

By varying the overall length of the drive coupling 134 by varying the length of the interchangeable drive coupling 134a, the initial start position (before actuation of the trigger) of a proximal end 240 (the end nearest the discharge needle 118 of the syringe 114) of the drive coupling 134 can be varied. Hence, the proximal end 240 can be arranged to have an initial start position as close as possible to the contents of the syringe—i.e. the initial volume of the syringe 114 can correspond substantially to the volume of the syringe contents. This way, the clearances which have to be taken up when the drive 130 is first released can be minimised, thereby reducing noise and recoil in the injection device 110.

Hence, a smaller volume of liquid in the syringe requires a longer interchangeable drive coupling 134a.

Since the length of the drive coupling 134 is variable, it follows that the point at which the flexible latch arms no longer couple the drive element 132 to the drive coupling 134 needs to be varied to ensure that the contents of the syringe can be completely discharged. This is done by varying the length of the interchangeable release element 155.

The longer the drive coupling 134 is, the longer interchangeable release element 155 needs to be.

The interchangeable release element 155 is provided with flexible arms 271 for connecting the interchangeable release element 155 to the syringe carrier 150 at cut-outs 281 on the syringe carrier 150.

Figure 4:
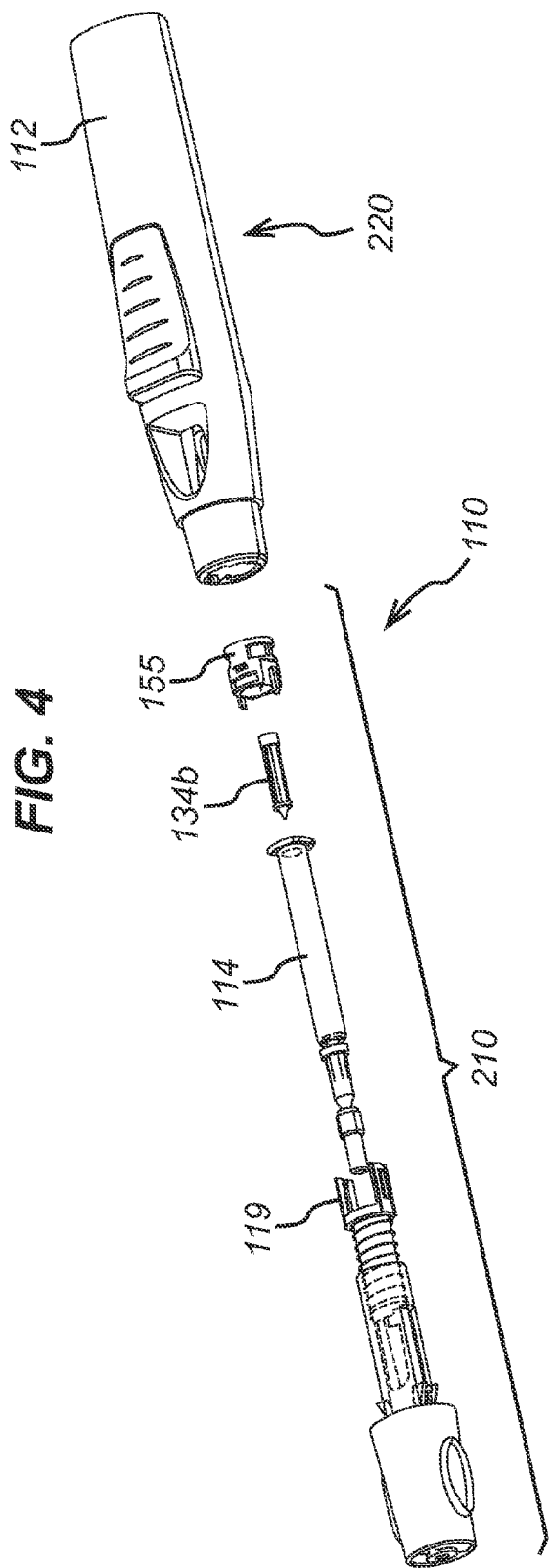
FIG. 4 shows a perspective view of sub-assemblies of the injection device according to the present invention.

As shown in FIG. 4, the injection device 110 can be assembled in two sub-assemblies for ease of manufacture.

A first sub-assembly 210 comprises inserting the syringe 114, syringe carrier 150, interchangeable drive coupling 134b and interchangeable release element 155.

A second sub-assembly 220 comprises the housing 112 and drive elements and actuators of the injection device 110, including the fixed length drive coupling 134a.

This way, a decision on the amount of contents to be inserted into the syringe can be made independently of the construction of the drive elements (which are difficult to assemble) because the length of interchangeable drive coupling 134b and interchangeable release element 155 can be varied immediately before final assembly of the complete injection device 110 by combining the first sub-assembly 210 with the second sub-assembly 220.

It will of course be understood that the present invention has been described above purely by way of example and modifications of detail can be made within the scope of the invention.

What is claimed is:

1. An injection device comprising:
   a housing adapted to receive a syringe having a discharge nozzle and a dispensing piston movable in the syringe to expel the contents of the syringe through the discharge nozzle;
   a drive adapted on activation to act on the syringe to advance it from a retracted position in which the discharge nozzle is contained within the housing to an extended position in which the discharge nozzle extends from the housing;
   a drive coupling for extending from the drive to the dispensing piston of the syringe so as to transfer movement of the drive to the piston;
   wherein the drive coupling comprises a fixed-length drive coupling and an interchangeable drive coupling and;
   an interchangeable release element adapted to actuate after a predetermined amount of movement of the dispensing piston a delay mechanism in the drive acting on the fixed-length drive coupling.

2. The injection device of claim 1, wherein the interchangeable drive coupling comprises a rigid member configured to connect with the dispensing piston and with the fixed-length drive coupling.

3. The injection device of claim 2, wherein the rigid member has a longitudinal axis.

4. The injection of claim 3, wherein the quantity of the contents of the syringe which is expelled in use determines the length of the interchangeable drive coupling along its longitudinal axis.

5. The injection device of claim 4, wherein the length of the interchangeable drive coupling is inversely proportional to the quantity of the contents of the syringe.

6. The injection device of claim 1, wherein the interchangeable release element is a constriction adapted to act on at least one arm linking the fixed-length drive coupling to the drive, thereby releasing the drive from the fixed-length drive coupling.

7. The injection device of claim 6, wherein the length of the constriction determines the predetermined amount of movement of the piston.

8. The injection device of claim 7, wherein the length of the constriction is inversely proportional to the quantity of the contents of the syringe.

9. A method of manufacturing an injection device, comprising:
- inserting a syringe having a piston into a first sub-assembly;
- inserting an interchangeable drive coupling into the syringe to contact the piston;
- providing a second sub-assembly comprising a drive and a fixed-length drive coupling;
- connecting an interchangeable release element to the first sub-assembly, wherein the interchangeable release element is adapted to actuate after a predetermined amount of movement of the dispensing piston a delay mechanism in the drive acting on the fixed-length drive coupling;
- assembling the first sub-assembly and second sub-assembly together, wherein, on assembly, the fixed-length drive coupling and interchangeable drive coupling communicate in use to transfer movement of the drive to the piston to act on the syringe to advance it from a retracted position in which the discharge nozzle is contained within the housing to an extended position in which the discharge nozzle extends from the housing.

10. The method of claim 9, wherein the interchangeable component has a longitudinal axis and comprises a rigid member configured to connect with the piston and with the drive coupling.

11. The method of claim 9 or claim 10, further comprising selecting the interchangeable drive coupling in accordance with its length determined by the quantity of the contents of the syringe.

12. The method of claim 9, further comprising selecting the interchangeable release element in accordance with its length determined by the quantity of the contents of the syringe.

* * * * *